(12) United States Patent
Birnboim

(10) Patent No.: US 10,619,187 B2
(45) Date of Patent: *Apr. 14, 2020

(54) COMPOSITIONS AND METHODS FOR OBTAINING NUCLEIC ACIDS FROM SPUTUM

(71) Applicant: DNA GENOTEK INC., Kanata (CA)

(72) Inventor: H. Chaim Birnboim, Ottawa (CA)

(73) Assignee: DNA GENOTEK INC., Ottawa (CA)

(*) Notice: Subject to any disclaimer, the term of this patent is extended or adjusted under 35 U.S.C. 154(b) by 351 days.

This patent is subject to a terminal disclaimer.

(21) Appl. No.: 15/345,420

(22) Filed: Nov. 7, 2016

(65) Prior Publication Data

US 2017/0152545 A1 Jun. 1, 2017

Related U.S. Application Data

(63) Continuation of application No. 14/549,344, filed on Nov. 20, 2014, now Pat. No. 9,523,115, which is a
(Continued)

(51) Int. Cl.
*C12Q 1/6806* (2018.01)
*B01L 3/00* (2006.01)
*C12N 15/10* (2006.01)

(52) U.S. Cl.
CPC .......... *C12Q 1/6806* (2013.01); *B01L 3/502* (2013.01); *B01L 3/5082* (2013.01);
(Continued)

(58) Field of Classification Search
CPC ..... C12Q 1/6806; B01L 3/5082; B01L 3/502; B01L 2300/047; B01L 2300/046;
(Continued)

(56) References Cited

U.S. PATENT DOCUMENTS 5,140,043 A 8/1992 Darr et al.
5,364,763 A 11/1994 Kacian
(Continued)

FOREIGN PATENT DOCUMENTS

CA 2072331 A1 12/1992
CA 2236240 A1 10/1999
(Continued)

OTHER PUBLICATIONS

Birnboim (1971) "New Method for Extraction of Ribonucleic Acid and Polyribosomes from Schizosaccharomyces pombe," Journal of Bacteriology. 107(3):659-663.
(Continued)

*Primary Examiner* — Sally A Merkling
(74) *Attorney, Agent, or Firm* — Lathrop GPM LLP; James H. Velema, Esq.

(57) ABSTRACT

The present invention relates to compositions and methods for preserving and extracting nucleic acids from saliva. The compositions include a chelating agent, a denaturing agent, buffers to maintain the pH of the composition within ranges desirable for DNA and/or RNA. The compositions may also include a reducing agent and/or antimicrobial agent. The invention extends to methods of using the compositions of the invention to preserve and isolate nucleic acids from saliva as well as to containers for the compositions of the invention.

36 Claims, 11 Drawing Sheets

Related U.S. Application Data continuation of application No. 12/338,873, filed on Dec. 18, 2008, now abandoned, which is a continuation of application No. 10/455,680, filed on Jun. 5, 2003, now Pat. No. 7,482,116.

(60) Provisional application No. 60/386,399, filed on Jun. 7, 2002, provisional application No. 60/386,397, filed on Jun. 7, 2002, provisional application No. 60/386,398, filed on Jun. 7, 2002.

(52) U.S. Cl.
CPC .... *C12N 15/1003* (2013.01); *B01L 2300/042* (2013.01); *B01L 2300/046* (2013.01); *B01L 2300/047* (2013.01); *B01L 2300/0672* (2013.01); *B01L 2300/0832* (2013.01); *B01L 2400/0683* (2013.01)

(58) Field of Classification Search
CPC ....... B01L 2300/0672; B01L 2300/042; B01L 2300/0832; B01L 2400/0683; C12N 15/1003
See application file for complete search history.

(56) References Cited

U.S. PATENT DOCUMENTS

| | | | |
|---|---|---|---|
| 5,496,562 | A | 3/1996 | Burgoyne |
| 5,807,527 | A | 9/1998 | Burgoyne |
| 5,817,630 | A | 10/1998 | Hofmann et al. |
| 5,827,675 | A | 10/1998 | Skiffington et al. |
| 6,176,836 | B1 | 1/2001 | Trudil et al. |
| 6,242,188 | B1 | 6/2001 | Dattagupta et al. |
| 6,291,178 | B1 | 9/2001 | Schneider |
| 6,309,827 | B1 | 10/2001 | Goldstein et al. |
| 6,428,962 | B1 | 8/2002 | Naegele |
| 6,503,716 | B1 | 1/2003 | Lai et al. |
| 6,551,777 | B1 | 4/2003 | Shuber et al. |
| 6,617,170 | B2 | 9/2003 | Augello et al. |
| 6,716,392 | B1 | 4/2004 | Putcha et al. |
| 6,869,769 | B2 | 3/2005 | Burgoyne |
| 7,482,116 | B2 | 1/2009 | Birnboim |
| 8,158,357 | B2 | 4/2012 | Birnboim et al. |
| 8,221,381 | B2 | 7/2012 | Muir et al. |
| 9,523,115 | B2 | 12/2016 | Birnboim |
| 2001/0008614 | A1 | 7/2001 | Aronowitz |
| 2002/0026046 | A1 | 2/2002 | Pasloske et al. |
| 2002/0081575 | A1 | 6/2002 | Small et al. |
| 2002/0197631 | A1* | 12/2002 | Lawrence ............... B01L 3/502 435/270 |
| 2006/0139631 | A1 | 6/2006 | Feldsine et al. |
| 2009/0162866 | A1 | 6/2009 | Birnboim |
| 2009/0162924 | A1 | 6/2009 | Birnboim |
| 2011/0212002 | A1 | 9/2011 | Curry et al. |
| 2012/0061392 | A1 | 3/2012 | Beach et al. |

FOREIGN PATENT DOCUMENTS

| | | |
|---|---|---|
| EP | 0 586 024 B1 | 3/1994 |
| EP | 0 734 684 A1 | 10/1996 |
| FR | 2279378 A1 | 2/1976 |
| FR | 2279378 A * | 3/1976 |
| WO | 1989/006704 A1 | 7/1989 |
| WO | 1991/002740 A1 | 3/1991 |
| WO | 1997/005248 A2 | 2/1997 |
| WO | 1998/044158 A1 | 10/1998 |
| WO | 1999/029904 A2 | 6/1999 |
| WO | WO-99/29904 A2 * | 6/1999 |
| WO | 2001/034844 A1 | 5/2001 |
| WO | 2001/060517 A2 | 8/2001 |
| WO | 2002/044691 A2 | 6/2002 |
| WO | 2003/104251 A2 | 12/2003 |
| WO | 2004/033470 A2 | 4/2004 |

OTHER PUBLICATIONS

Birnboim (1992) "Effect of Lipophilic Chelators on Oxyradical-Induced DNA Strand Breaks in Human Granulocytes: Paradoxical Effect of 1,1 O-Phenanthroline," Archives of Biochemistry and Biophysics. 294(1):17-21.

Birnboim (1992) "Extraction of High Molecular Weight RNA and DNA from Cultured Mammalian Cells," Methods in Enzymology. 216:154-160.

Birnboim et al. (1979) "A rapid alkaline extraction procedure for screening recombinant plasmid DNA," Nucleic Acids Research. 7(6):1513-1524.

Birnboim et al. (1981) "Fiuorometric Method for Rapid Detection of DNA Strand Breaks in Human White Blood Cells Produced by Low Doses of Radiation," Cancer Research. 41:1889-1892.

Buettner (1986) "Ascorbate Autoxidation in the Presence of Iron and Copper Chelates," Free Radical Research Communications, Free Radical Research Communications. 1:349-353.

Buettner (1988) "In the absence of catalytic metals ascorbate does not autoxidize at pH 7: ascorbate as a test for catalytic metals," Journal of Biochemical and Biophysical Methods. 16:27-40.

Buettner (1990) "Ascorbate oxidation: UV absorbance of ascorbate and ESR spectroscopy of the ascorbyl radical as assays for iron," Free Radical Research Communications. 10:5-9.

Buettner et al. (1996) "Catalytic Metals, Ascorbate and Free Radicals: Combinations to Avoid," Radiation Research. 145:532-541.

Clarke et al. (1991) "Stabilities of the alkaline earth and divalent transition metal complexes of the tetraazamacrocyclic tetraacetic acid ligands," Inorganic Chimica Acta. 190:27-36.

Croxson et al. (1981) "Extraction of Rotavirus from Human Feces by Treatment with Lithium Dodecyl Sulfate," Applied and Environmental Microbiology. 41(1)255-260.

Dawson et al. (1989) "Stability constants of metal complexes," Ch. 17 in; Data for Biochemical Research, Third Edition, Oxford Science Publications. pp. 399-407.

Garcia-Closas et al. (2001) "Collection of Genomic DNA from Adults in Epidemiological Studies by Buccal Cytobrush and Mouthwash," Cancer Epidemiology, Biomarkers & Prevention. 10:687-696.

Heath et al. (2001) "Use of Buccal Cells Collected in Mouthwash as a Source of DNA for Clinical Testing," Arch. Pathol. Lab. Med. 125:127-133.

Loens et al. (2002) "Detection of Mycoplasma pneumoniae in Spiked Clinical Samples by Nucleic Acid Sequence-Based Amplification," Journal of Clinical Microbiology. 40(4):1339-1345.

Lum (1998) "A Simple Mouthwash Method for Obtaining Genomic DNA in Molecular Epidemiological Studies," Cancer Epidemiology, Biomarkers & Prevention. 7:719-724.

Pershadsingh et al. (1980) "A High Affinity Calcium-stimulated Magnesium-dependent Adenosine Triphosphatase in Rat Adipocyte Plasma Membranes," The Journal of Biological Chemistry. 255(9):4087-4093.

Rahman et al. (2004) "Chromatography Paper Strip Method for Collection, Transportation, and Storage of Rotavirus RNA in Stool Samples," Journal of Clinical Microbiology. 42(4):1605-1608.

Rymaszewski et al. (1990) "Estimation of Cellular DNA Content in Cell Lysates Suitable for RNA Isolation," Analytical Biochemistry. 188:91-96.

Smith et al. (2003) "Potent Inhibition of Ribonuclease A by Oligo(vinylsulfonic Acid)," Journal of Biological Chemistry. 278:20934-20938.

Terasaki et al. (1998) "Saliva as DNA Source for HLA Typing," Human Immunology. 59:597-598.

Van Schie et al. (1997) "Saliva: a convenient source of DNA for analysis of bi-allelic polymorph isms of Fcg receptor I IA (CD32) and Fcg receptor IIIB (CD16)," Journal of Immunological Methods. 208:91-101.

Wollants et al. (2004) "Evaluation of a norovirus sampling method using sodium dodecyl sulfate/EDT A-pretreated chromatography paper strips," Journal of Virological Methods. 122:45-48.

European Office Action corresponding to European Patent Application No. 03729743, dated Oct. 1, 2007.

(56) References Cited

OTHER PUBLICATIONS

International Preliminary Report corresponding to International Patent Application No. PCT/CA2007/001785, dated Jan. 19, 2009.
International Search Report corresponding to International Patent Application No. PCT/CA03/00869, dated Mar. 30, 2004.
International Search Report with Written Opinion corresponding to International Patent Application No. PCT/CA2007/001785, dated Jan. 21, 2008.
Response to the Written Opinion corresponding to International Patent Application No. PCT/CA2003/000869, dated Jun. 3, 2004.
Written Opinion corresponding to International Patent Application No. PCT/CA2003/000869, dated Apr. 5, 2004.
U.S. Appl. No. 10/455,680 / 2004/0038269 / U.S. Pat. No. 7,482,116, filed Jun. 5, 2003 / Feb. 26, 2004 / Jan. 27, 2009, H. Chaim Birnboim.
U.S. Appl. No. 10/338,848 / 2009/0162924, filed Dec. 18, 2008 / Jun. 25, 2009, H. Chaim Birnboim.
U.S. Appl. No. 12/338,873 / 2009/0162866, filed Dec. 18, 2008 / Jun. 25, 2009, H. Chaim Birnboim.
U.S. Appl. No. 14/549,344 / 2015/0104803 / U.S. Pat. No. 9,523,115, filed Nov. 20, 2014 / Apr. 16, 2015 / Dec. 20, 2016, H. Chaim Birnboim.
U.S. Appl. No. 15/345,420, filed Nov. 7, 2016, H. Chaim Birnboim.

* cited by examiner

Ascorbate anion

Ascorbate radical

Dehydroascorbic acid

COMPOSITIONS AND METHODS FOR OBTAINING NUCLEIC ACIDS FROM SPUTUM

CROSS-REFERENCE TO RELATED APPLICATIONS

This application is a continuation of U.S. patent application Ser. No. 14/549,344, filed Nov. 20, 2014, which is a continuation of U.S. patent application Ser. No. 12/338,873, filed Dec. 18, 2008, which is a continuation of U.S. patent application Ser. No. 10/455,680, filed Jun. 5, 2003, now U.S. Pat. No. 7,482,116, which claims the benefit of U.S. Provisional Patent Application Ser. No. 60/386,397, filed Jun. 7, 2002, U.S. Provisional Patent Application Ser. No. 60/386,398, filed Jun. 7, 2002, and U.S. Provisional Patent Application Ser. No. 60/386,399, filed Jun. 7, 2002, each of which is hereby incorporated herein by reference in its entirety.

BACKGROUND OF THE INVENTION

The present invention relates to compositions and methods for preserving nucleic acids at room temperature for extended periods of time and for simplifying the isolation of nucleic acids.

DNA can be extracted from virtually every type of cell in the human body, with the exception of red blood cells. The usual source of bodily samples for extraction of DNA is venous blood, since the number of nucleated white blood cells (principally neutrophils and lymphocytes) is relatively high and quite consistent: the normal range is about 5 to 10 million white blood cells per milliliter of blood. The DNA content of human cells is about 6 micrograms per million cells, so 1 milliliter can theoretically yield from 30 to 60 micrograms of DNA. However, there are about 5 billion red blood cells per milliliter of blood, which, since they contain no DNA, must be removed to obtain pure DNA. Furthermore, the use of blood as a source of DNA has many other disadvantages. Collection of blood is not a trivial procedure. Taking of venous blood requires trained personnel. It is an invasive procedure, which frequently causes some distress and pain to the donor. Precautions are needed to minimize exposure of personnel to blood-borne pathogens. Once collected, the blood sample must be either frozen or quickly transported to a laboratory for extraction of DNA. For these reasons, venous blood is not the ideal source of DNA. A simpler procedure for obtaining blood is to collect a few drops after a finger prick and blotting it onto a piece of filter paper. Less training of personnel is required. Once dried, the DNA is quite stable. The amount of DNA recovered is small but sufficient for many forensic purposes. However, a finger prick is still an invasive procedure and heme derived from hemoglobin in blood can inhibit some types of DNA analysis.

Swabbing the inside of the cheek with a brush (a buccal swab) is another source of cells that contain DNA. It is much less invasive than taking of blood and can be collected by individuals with less training than is required in the collection of blood. Once collected, the time that useable DNA can be recovered can be extended by either drying the swab or wiping onto filter paper and drying it. However, as the inside of the mouth is not a sterile source (as compared to blood) and microbes can degrade the quality of the DNA after a period of time. The number of cells recovered by this procedure is not large and typically less than 1-2 micrograms of DNA can be expected in the entire sample.

Saliva is a fairly clear, colorless fluid secreted principally by the major salivary glands (parotid, submandibular, and sublingual). Its function is to lubricate and cleanse the oral cavity, as well as to initiate the process of digestion. The parotid gland primarily secretes serous (watery) saliva, while the other glands secrete a mixture of serous and mucinous (sticky) saliva. Components of saliva include albumin, globulin, mucins, and digestive enzymes. It has long been known that cellular DNA is present in saliva and that this DNA is suitable for forensic purposes. Forensic use is typically limited to victim or suspect identification, using the tiny amounts of DNA from saliva that may recovered at a crime scene or from the back of a postage stamp. The notion that saliva may be a reliable source of genomic DNA and a rival to venous blood samples for this purpose has been investigated more recently in a scientific publication (van Schie, et al., *J. Immunol. Methods* 208:91-101, 1997). The authors used freshly collected or frozen saliva samples and purified the DNA by a fairly complex extraction procedure. Estimates of the quantity of DNA recovered were based upon light absorption at 260 nm, a procedure known to be an unreliable method since other common biological macromolecules, such as RNA, have essentially the same ultraviolet light absorption spectrum. Nevertheless, these authors showed that quality genomic DNA was indeed present by gel electrophoretic analysis and polymerase chain reaction analysis for certain allelic polymorphisms. Another communication (Terasaki, et al., *Hum. Immunol.* 59:597-598, 1998) reported similar results about the suitability of saliva as a source of DNA for HLA typing by polymerase chain reaction analysis. Although the amount of DNA recovered was reported, the method used to measure DNA was not. These authors provided 3 examples where saliva dried on filter paper yielded DNA suitable for analysis.

With the increasing use of DNA-based analysis in forensics, law enforcement, military, human medicine, veterinary medicine, and research, there is a need for a product that would allow saliva to become a standard reliable source of DNA from an individual (to replace blood, the current standard). In forensic, military and mass disaster situations, for example, DNA samples are now routinely taken from living persons thought to be relatives of unidentified victims of accident or foul play, to aid in identification of the dead. Military personnel or other individuals who expect to encounter hazardous situations where their lives may be at risk may wish to store DNA samples prior to exposing themselves to these hazards. In the law enforcement area, convicted felons in both Canada and the United States are now required to provide DNA samples. DNA-based tests are expected to increase in medicine, such as testing for cystic fibrosis, cytochrome P450 isotypes, polymorphisms affecting susceptibility to infectious and autoimmune diseases, HLA typing, paternity issues, to name but a few. In clinical studies, an example would be to screen populations for colon cancer-predisposing genes or family members of a breast cancer victim for breast cancer predisposing genes. In all of these cases, there are significant advantages to providing a saliva sample rather than providing a blood sample as a source of DNA. All donors would prefer donating saliva rather than blood because of the discomfort, pain, or apprehension associated with phlebotomy or pin-pricks. Saliva has a further advantage of not requiring specialized personnel thereby reducing cost where mass sample collection is being carried out. The risk of blood-borne infection is likewise decreased.

In addition to the problem of developing a standard collection and preservation method for DNA in saliva, there remains an ongoing need to improve methods of overcoming problems specific to the recovery of nucleic acids from saliva. The problem of extraction of high molecular weight DNA and RNA from mammalian cells has been partially addressed by Bimboim in *Methods of Enzymology* 216:154-160, 1993, but this work was not extended to the recovery of nucleic acids from mucin-containing bodily fluids.

Multimeric proteins called mucins are high molecular weight glycosylated proteins that form a major part of a protective biofilm on the surface of epithelial cells, where they can provide a barrier to particulate matter and bind microorganisms. These glycoproteins contribute greatly to the viscoelastic nature of saliva. The major high-molecular-weight mucin in salivary secretions is MUC5B, one of four gel-forming mucins that exist as multimeric proteins with molecular weights greater than 20-40 million daltons. MUC5B is a large oligomeric mucin composed of disulphide-linked subunits.

It is known that reagents that reduce disulfides also reduce the viscosity of mucin, such as that found in sputum or saliva. Reducing agents, in particular sulfur-containing chemicals such as β-mercaptoethanol and dithiothreitol, are widely used in biochemistry. However, many biochemically relevant reducing agents are capable of reacting in solution with dissolved oxygen. This is known are autoxidation (also called autooxidation or autooxidation), where 1-electron reduction intermediates of oxygen are formed, viz., superoxide ($O_2^-$), hydrogen peroxide ($H_2O_2$) and hydroxyl radical (OH). In addition, transitional metal cations function as catalysts and $O_2^-$ has been demonstrated to be an intermediate. Unfortunately, reducing agents and reducing compositions of the prior art have a relatively short shelf life, especially in basic solutions, and stock solutions that contain reducing agents cannot be prepared and stored under ambient conditions for an extended period time, usually not more than a day or two.

Therefore, in addition to a need for a means to collect sputum or saliva, and subsequently preserving the nucleic acids contained therein by contacting them with a stabilizing composition, there is a need for the inclusion of a stable reducing agent into the composition, such that nucleic acids can be conveniently recovered from it, especially after extended periods of time in the presence of oxygen at neutral or mildly alkaline pH.

SUMMARY OF THE INVENTION

The present inventor has developed a composition, which, when mixed with a mucin-containing bodily fluid, preserves the nucleic acids at room temperature under ambient conditions for extended periods of time. There is no requirement for freezing of the samples before nucleic acid recovery and purification. The properties of this composition are that it (a) chemically stabilizes nucleic acids, (b) inhibits nucleases that may be present in the saliva, and (c) is compatible with proteolytic enzymes and other reagents used to purify/amplify oligo- or polynucleotides. A fourth and novel property of this composition is that it contains an agent that rapidly reduces the viscous properties of mucin, greatly facilitating the extraction of nucleic acids contained within.

Accordingly, a first aspect of the invention features a composition for preserving nucleic acids that includes a chelating agent, and a denaturing agent, where the pH of the composition is greater than 5.0. In one embodiment, the composition is an aqueous solution.

In another embodiment, the composition also includes a reducing agent. For example, it can include one or more of the following: ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof. Desirably, the reducing agent is ascorbic acid, erythiorbate, N-acetylcysteine, dithiothreitol, or 2-mercaptoethanol, and most desirably, the reducing agent is ascorbic acid. In another embodiment, the composition does not contain ascorbic acid. In yet another embodiment, the concentration of the reducing agent in the composition is greater than or equal to 50 millimolar.

Antioxidant free-radical scavengers are also desirable reducing agents for the composition of the present invention. Examples include antioxidant vitamins, antioxidant hormones, antioxidant enzymes, thiols, and phenols.

Desirably, the reducing agent retains reducing activity for at least 46 days in the presence of one or more of the following: oxygen, ambient air, ambient light, and alkaline pH.

The chelating agent of the composition can be selected from the group consisting of: ethylenediamine tetraacetie acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), and desferrioximine, or chelator analogs thereof. Desirably, the chelating agent is cyclohexane diaminetetraacetate (CDTA), diethylenetriamine pentaacctic acid (DTPA), tctraazacyclododecanetetraacetic acid (DOTA), or desferrioximine, and most desirably, the chelating agent is cyclohexane diaminetetraacetate (CDTA).

In another embodiment, the chelating agent of the composition inhibits metal redox cycling. By "inhibits metal redox cycling" is meant the inhibition of metal-based oxidation/reduction cycles that produce reactive oxygen free-radical species. Examples of redox ion pairs involved in such cycles include $Fe^{2+}/Fe^{3+}$, $Cu^{1+}/Cu^{2+}$, and various oxidation states of molybdenum, vanadium, nickel, and cobalt. Chelators that bind one or both ions of a redox ion pair can inhibit the production of reactive oxygen species such as, for example, hydroxyl radical (HO.), hydroperoxyl radical (HOO.), superoxide radical ($O_2^-$.), nitric oxide radical (NO.), or peroxynitrite radical ($ONO_2^-$.).

The nucleic acid to be preserved by the composition can be DNA or RNA, including mRNA or viral RNA.

The pH of the composition can between from about 5.0 and about 11.0, desirably from about 6.5 to about 7.5, and most desirably, about 7.0. For the preservation of DNA, a pH from about 7.0 to about 10.0 can be used. Depending on other components of the compositions, desirable pHs are about 7.5, about 8.0, or a pH range from about 8.0 to about 9.0. A buffer, such as HEPES, TRIS, or carbonate buffer can be added to the composition to maintain the pH in a constant range. For the preservation of RNA, a pH from about 5.0 to about 7.0, desirably from about 6.5 to about 6.8 can be used. Again, a buffer, such as BES, can be used to maintain the pH in a constant range.

The denaturing agent of the composition can be selected from the group consisting of: urea, dodecyl sulfate, guanidinium chloride, guanidinium thiocyanate, perchlorate, and an alcohol. Desirably, the denaturing agent is urea, dodecyl sulfate, or an alcohol, wherein the alcohol is 10%-60% of the total composition volume. The alcohols can be methanol, ethanol, n-propanol, isopropanol, n-butanol, trifluoroethanol, phenol, or 2,6-di-tert-butyl-4-methylphenol.

In another embodiment, the composition includes an antimicrobial agent. By "antimicrobial agent" is meant a substance or group of substances which reduces the rate of growth of an organism compared to the rate of growth of the organism in their absence. A reduction in the rate of growth of an organism may be by at least 5%, more desirably, by at least 10%, even more desirably, by at least 20%, 50%, or 75%, and most desirably, by 90% or more. The definition also extends to substances which affect the viability, virulence, or pathogenicity of an organism. An antimicrobial agent can be natural (e.g., derived from bacteria), synthetic, or recombinant. An antimicrobial agent can be bacteriostatic, bactericidal or both. An antimicrobial agent is bacteriostatic if it inhibits cell division without affecting the viability of the inhibited cell. An antimicrobial agent is bactericidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is bacteriostatic at a given concentration may be bactericidal at a higher concentration. Certain bacteriostatic substances are not bactericidal at any concentration. Desirably, the composition of the invention includes an alcohol as an antimicrobial agent, and most desirably the composition includes ethanol.

In another embodiment, the composition also includes an inhibitor of ribonuclease. Desirable inhibitors are selected from the group consisting of: heparin, heparan sulfate, oligo(vinylsulfonic acid), poly(vinylsulfonic acid), oligo(vinylphosphonic acid), and poly(vinylsulfuric acid), or salts thereof. The inclusion of an inhibitor of ribonuclease in the composition of the invention is particularly desirable when the nucleic acid to be preserved is RNA, desirably mRNA, or when the nucleic acid to be preserved is from a virus or a bacterium.

A second aspect of the invention features a method of reducing the viscosity of a mucin-containing bodily fluid or tissue by reducing disulfide bonds inherent to mucin, wherein the bodily fluid or tissue is mixed with a composition of the invention that includes a reducing agent. In one embodiment, the bodily fluid is sputum, desirably saliva. By "sputum" is meant that mucoid matter contained in or discharged from the nasal or buccal cavity of an animal, including saliva and discharges from the respiratory passages, including the lungs. In another embodiment, the method includes the recovery of a nucleic acid.

A third aspect of the invention features a method of preserving a nucleic acid contained in sputum that includes the steps of obtaining sputum from a subject, and contacting the sputum with a composition of the invention, thus preserving the nucleic acid.

In one embodiment, when the nucleic acid is DNA, the DNA is stable for more than 14 days, desirably more than 30 days, and more desirably more than 60 days. In another embodiment, when the nucleic acid is DNA and the composition does not contain ascorbic acid, the DNA is stable for more than 60 days, and desirably more than 360 days.

A fourth aspect of the invention features a method of recovering a nucleic acid from sputum that includes the steps of: i) obtaining sputum from a subject, ii) contacting the sputum with a composition of the invention to form a mixture, iii) contacting the mixture with a protease, and iv) recovering the nucleic acid from the mixture. Desirably, the protease is proteinase K or pronase.

In one embodiment of any of the second, third, or fourth aspects, the sputum is saliva. In another embodiment, the sputum is from a mammal, desirably a human. In yet another embodiment, the nucleic acid is DNA or RNA. If the nucleic acid is RNA, desirably it is mRNA or viral RNA. The nucleic acid can be from a source foreign to the subject from which the sputum sample is taken. For example, the nucleic acid can be from a bacterium or a virus that is residing in the buccal, nasal, or respiratory passages of the subject.

In a fifth aspect, the invention features a method of preserving and/or recovering a nucleic acid from a bodily fluid that includes, placing the bodily fluid into a first region of a container, placing a composition of the invention into a second region of the container, which is separated from the first region by a barrier, closing the container, and disturbing the integrity of the barrier such that the composition and the bodily fluid are brought into contact.

In one embodiment, the disestablishment of the barrier is coupled to the closing of the container when a lid is placed on it. In one example, the barrier is punctured. In a desirable example, the barrier is in the form of a pivoting sealing disc. In this example, attachment of the lid to the container forces the disc to pivot from its original position of spanning the space between the first region and the second region to a position in which both regions are exposed to each other, thereby forming a mixture between a composition of the invention and the bodily fluid is allowed. Desirably, the bodily fluid is sputum, and most desirably, saliva.

In a sixth aspect, the invention features a device for preserving and/or isolating a nucleic acid obtained from a biological sample. The device includes: a container that has a first region for collecting a biological sample and a second region containing a composition for preserving a nucleic acid, a barrier between the first region the second region that keeps the biological sample and the composition separate, a means for closing the container, and a means for disturbing the integrity of the barrier such that the composition is capable of contacting the biological sample. The first region can have an opening of from 2.0 to 7.0 cm, desirably from 2.5 to 3.5 cm, and most desirably 3.0 cm. Desirably, the biological sample is sputum, and most desirably, saliva.

In one embodiment of the sixth aspect, the nucleic acid-preserving composition is a composition of the present invention. In another embodiment, the means for closing the container is coupled to the means for disturbing the integrity of the barrier. In yet another embodiment, the means for closing the container is an airtight lid.

In a seventh aspect, the invention features a method of manufacturing a device for preserving a nucleic acid in a biological sample that includes: providing a container that has a first region and a second region, with the first region suitable for containing a composition of the invention and the second region having an opening suitable for the application of a biological sample; placing the composition into the first region; and applying a barrier to the container between the first region and the second region, with the barrier being impermeable to the composition and capable of being disestablished.

In an embodiment of either the sixth or seventh aspect, the barrier can be a pivoting disc, where in a first position, the disc spans the compartment and separates the first and second areas. Pivoting the disc to a second position (e.g., by connecting a screw-on lid to a plunger mechanism which contacts the disc, causing it to pivot when the lid is screwed on) disestablishes the barrier and allows the biological sample contained in the first region to contact the composition that is contained in the second region.

By "about" is meant +/−10% of the stated value or a chemical or obvious equivalent thereof.

By "alcohol" is meant a water-miscible organic compound containing a hydroxyl group, including water-miscible mixtures of hydroxyl-containing organic compounds.

By "antioxidant free-radical scavenger" is meant a substance that reduces a reactive oxygen free radical species. Such free radicals include, for example, hydroxyl radical (HO), hydroperoxyl radical (HOO.), superoxide radical ($O_2^-$.), nitric oxide radical (NO.), or peroxynitrite radical ($ONO_2^-$.).

By "aqueous solution" is meant a solution or suspension that contains 30% or more water by volume.

By "bodily fluid" is meant a naturally occurring fluid from an animal, such as saliva, serum, plasma, blood, urine, mucus, gastric juices, pancreatic juices, semen, products of lactation or menstration, tears, or lymph.

By "biological sample" is meant any sample containing nucleic acids that has been obtained from or deposited by an animal. Non-limiting examples include skin, hair, bodily fluids, fecal matter, and tissue.

By "chelator analog" is meant a derivative chelator compound with the same backbone structure and having the same general properties as the parent chelator compound.

By "denaturing agent" is meant a substance that alters the natural state of that to which it is added.

By "mucin" is meant any mucoprotein that raises the viscosity of the medium surrounding the cells that secrete it.

By "mucoid" is meant any bodily fluid containing mucin.

By "nucleic acid" is meant a chain of the nucleotides, including deoxyribonucleic acid (DNA) or ribonucleic acid (RNA), typically found in chromosomes, mitochodria, ribosomes, bacteria, or viruses.

By "nucleic acid-preserving composition" is meant any composition of the present invention, unless otherwise specified.

When referring to a nucleic acid, by "stable" is meant that at least about 50% of the initial amount of high molecular weight nucleic acid (DNA, RNA, mRNA, or viral RNA) contained in a sample is still present after storing the sample at ambient temperature (i.e., 20° C. to 25° C.) for the specified time period. The amount of high molecular weight DNA in a sample can quantified by densitometry analysis of the high molecular weight DNA band from an agarose gel (see FIG. 1 and Example 4).

By "resin-supported phosphine" is meant a polymer that contains a multiplicity of covalently-bound phosphine groups.

By "resin-supported thiol" is meant is meant a polymer that contains a multiplicity of covalently-bound sulfhydryl groups.

By "saliva" is meant the secretion, or combination of secretions, from any of the salivary glands, including the parotid, submaxillary, and sublingual glands, optionally mixed with the secretion from the buccal glands.

By "sputum" is meant that mucoid matter contained in or discharged from the nasal or buccal cavity of a mammal, including saliva and discharges from the respiratory passages, including the lungs.

By "subject" is meant any animal. Desirably, the subject is a mammal that can produce saliva for the purposes of nucleic acid extraction. Most desirably, the subject is a human.

Other features and advantages of the present invention will become apparent from the following detailed description. It should be understood, however, that the detailed description and the specific examples, while indicating preferred embodiments of the invention are given by way of illustration only, since various changes and modifications within the spirit and scope of the invention will become apparent to those skilled in the art from this detailed description.

DETAILED DESCRIPTION

Figure 1:
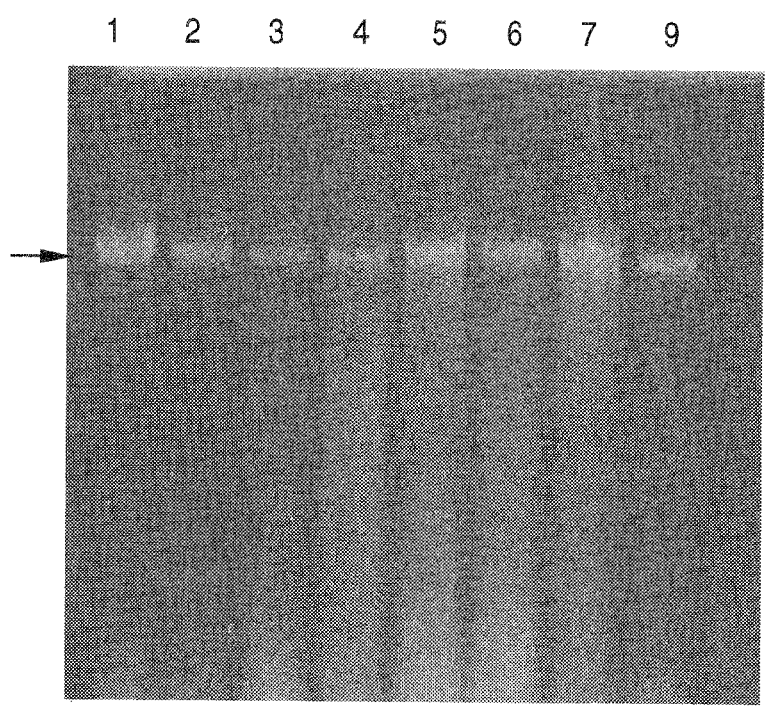
FIG. 1 is an electrophoresis agarose analysis of DNA isolated from saliva using the capacity of methods of one embodiment of the invention.

The following standard abbreviations are used herein: DNA, deoxyribonucleic acid; RNA, ribonucleic acid; mRNA, messenger RNA; HEPES, 4-(2-hydroxyethyl)-1-piperazineethanesulfonic acid; BES, N,N-bis[2-hydroxyethyl]-2-aminoethane-sulfonic acid; TRIS, tris(hydroxymethyl)aminomethane, CDTA, cyclohexane diaminetetraacetate; DTPA, N,N-bis(2-(bis(carboxymethyl)amino) ethyl)glycine; DOTA, 1,4,7,10-tetrazacyclododecanetetraacetic acid; and TETA, 1,4,8,11-tetraazacyclotetradecanetetraacetic acid.

Compositions of the Invention

The present inventors have developed compositions that render sputum as a viable option to the use of blood as a source of nucleic acids. The compositions provide the advantageous properties of chemical stabilization of nucleic acids and the inhibition of nucleases, including deoxyribonucleases, and microbial growth. Chemical stabilization of the nucleic acids in a saliva sample is achieved through the use of buffers to maintain an appropriate pH, as well as the use of chelating agents to prevent the phenomenon of metal redox cycling or the binding of metal ions to the phosphate backbone of nucleic acids. The chelating agents of the invention also participate in the inhibition of deoxyribonucleases and microbial growth, which can be additionally inhibited by the inclusion of denaturing agents and/or other suitable antimicrobial substances, such as ethanol, into the compositions of the invention. The compositions of the invention can also include one or more reducing agents, which can reduce sample viscosity, thereby making nucleic acid recovery an easier process.

Accordingly, the present invention features a composition for preserving and/or recovering nucleic acids from sputum, desirably saliva, that includes one or more chelators and one or more denaturing agents, wherein the pH of the composition is greater than 5, desirably within a pH range of about 6 to about 11, more desirably within a pH range of about 7.5 to about 10.0, and most desirably, within a pH of about 7.0.

The chemical backbone and the purine bases of DNA are most stable at slightly alkaline pH, with an optimal stability generally recognized as being within a pH range of about 7-11, and desirably a pH of about 8. Below a pH of about 6, depurination (i.e., spontaneous loss of purine bases from the deoxyribose-phosphate backbone) can occur. Above a pH of about 10, spontaneous loss of amino groups from cytosine nucleotides may occur, thereby converting cytosine to uracil. Above a pH of about 12, DNA is denatured, converting it from the double-strand form to the single-strand form. In contrast, RNA is most stable in the pH range of 5.0 to 7.0, desirably a pH of from 6.5 to 6.8. Accordingly, the pH of the composition may be adjusted using pH buffers, desirably those that best control the pH within the range of about 5 to about 11. Examples of pH buffers with desirable properties include, but not limited to, TRIS hydrochloride, HEPES and BES.

DNA has a strong affinity for metal ions, some of which, such as the common transition metals iron or copper, can catalyze the formation of reactive oxygen species. Therefore, a composition of the invention includes one or more chelators that can form complexes with metal ions to prevent them from binding to DNA, remove metal ions that that have already bound to DNA, or bind to metal ions (e.g., Fe(II)/Fe(III) or Cu(I)/Cu(II)) strongly enough to inhibit their redox cycling, and hence, the formation of reactive oxygen species. EDTA, a commonly used chelator in biological reagents, can be of some use for either of these purposes. More desirable are stronger chelators (i.e., chelators with a higher dissociation constant than EDTA when bound to a metal), used alone or in combination, that include, but are not limited to, CDTA, DTPA, DOTA, TETA, and desferioximine, or chelator analogs thereof. The amount or concentration of chelator will depend upon the strength of the chelator, which would need to be determined empirically. For CDTA, concentrations in the 1-20 mM range are sufficient, however other concentrations would work, and the compositions of the invention are not intending to be limited to this range.

Deoxyribonucleases and ribonucleases are enzymes that breakdown DNA or RNA, respectively. Their main source in the digestive tract is secretions of the pancreas, although lower levels may be present in cells of the salivary gland and buccal mucosa. In addition, microorganisms resident in the mouth or from recently ingested foods may contain deoxyribonucleases or ribonucleases. Pancreatic deoxyribonuclease is known to require divalent metal ions such as Mg(II), Mn(II) and/or Ca(II) for enzymatic activity. The strong chelators described above, in addition to providing chemical stability to the nucleic acids, will inhibit this class of metal ion-requiring deoxyribonucleases. The action of deoxyribonucleases and ribonucleases can also be inhibited by denaturing agents that will destroy the complex structures of these enzymes (proteins). Hence, denaturing agents are included in the nucleic acid preserving composition of the invention. Examples of denaturing agents that may be used (alone or in combination) include, but not limited to, urea, soluble salts of dodecyl sulfate and other strong detergents, guanidinium chloride, guanidinium thiocyanate, soluble salts of perchlorate, alcohols, such as ethanol, above 10%. Other reagents, such as heparin, heparan sulfate, or oligo (vinylsulfonic acid) (Smith, et al., *J. Biol. Chem. Mar.* 20, 2003; [epub ahead of print]) are known to inhibit the action of deoxynucleases and/or ribonucleases.

Low specificity proteases such as proteinase K are frequently used in the purification of nucleic acids. Since proteases are themselves proteins, their action can be inhibited by denaturing agents. Thus, a balance must be struck between the concentration of denaturing agents that will, on the one hand, inhibit deoxyribonucleases or ribonucleases and denature other proteins in saliva and, on the other hand, not significantly inhibit the proteolytic enzymes. At later stages in DNA purification, the DNA is often concentrated by precipitation with alcohol. Thus, salts, buffers, chelators and other components of the nucleic acid preserving/recovery solution must be chosen so as not to precipitate when concentrations of alcohol over 50% are added to precipitate the DNA.

The viscosity of sputum and saliva depends upon the presence of very high molecular weight glycoproteins complexes called mucins, particular the gel-forming mucins (Offner, et al., *Adv. Dent. Res.* 14:69-75, 2000; Seregni, et al., *Tumori* 83:625-632, 1997). It has been found that the inclusion of a reducing agent into a composition of the invention has the effect of markedly reducing the viscosity of saliva, especially "unstimulated" saliva, thereby facilitating the recovery of nucleic acids. Accordingly, in one embodiment, a composition of the invention further includes one or more reducing agents. The reducing agents are desirably at high concentration (greater than 0.05 M). While not wishing to be limited by theory, it is presumed that the reducing agent reduces the viscosity of the saliva by breaking disulfide bonds that hold together chains of mucin, and that any reducing agent that has the appropriate redox potential to reduce disulfide bonds in proteins would be suitable. Desirably, the reducing agent is selected from the group consisting of: ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof.

In another embodiment, a composition of the invention that includes a reducing agent maintains reducing capacity at room temperature in a sealed container in the presence of ambient oxygen, and/or in the presence of ambient light for more than a week, desirably for up to about 46 days, and most desirably for at least 46 days. This embodiment combines the nucleic acid stabilization provided by a strong chelator a denaturing agent, and a reducing agent in a composition with a pH within the range of about 6 to about 11, and desirably a pH of about 8.0.

Figure 5:
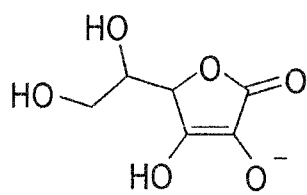
FIG. 5 shows structures of (oxidized) ascorbate anion, (reduced) dehydroascorbic acid, and a free radical intermediate
Figure 5:
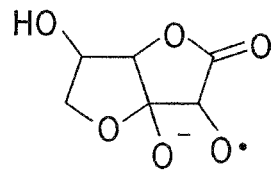
Figure 5:
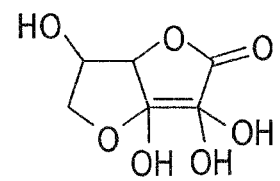
Figure 6:
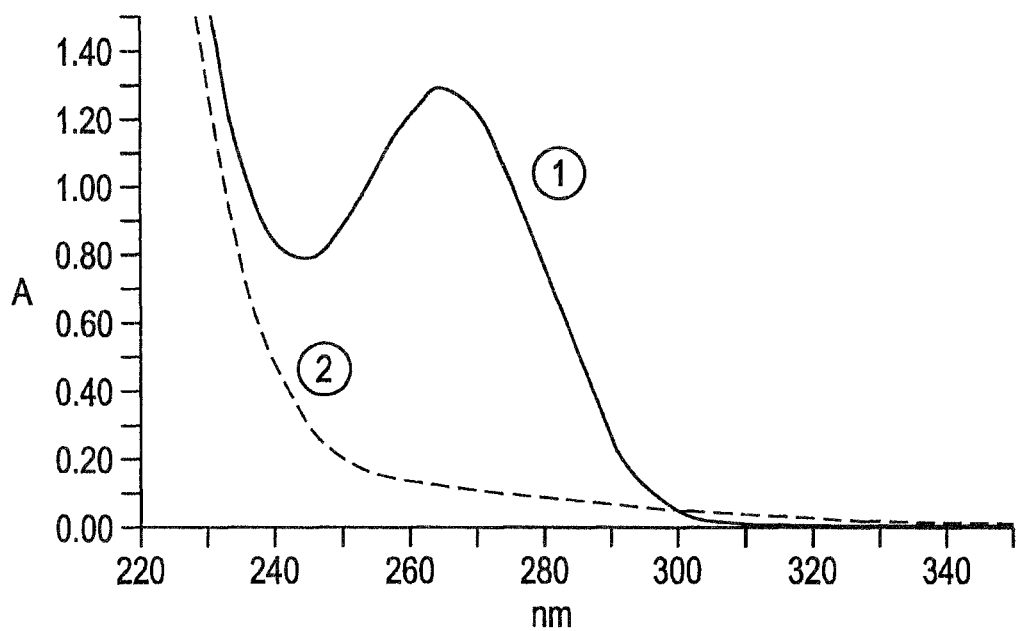
FIG. 6 is a compilation of two spectrophotometric scans of sodium ascorbate (100 μM) in CB (1 mM CDTA, 10 mM. BES, pH 7.4), prepared under aerobic conditions over 30 minutes at room temperature (scan 1) and 3 minutes after addition of a few crystals of $MnCl_2$. (scan 2), as per Example 8.

A particularly desirable reducing agent is sodium ascorbate. As well as an important dietary antioxidant micronutrient, ascorbic acid (vitamin C) is a non-thiol reducing agent and is inexpensive, non-toxic, and stable in the presence of the chelators and denaturing agents that are included in the compositions of the invention. The structures of (oxidized) ascorbate anion, (reduced) dehydroascorbic acid, and a free radical intermediate are shown in FIG. 5. The most thoroughly studied oxidation reaction of ascorbate is its oxidation by oxygen. As with many other reducing agents, trace amounts of transitional metals such as iron or copper can promote autooxidation (Buettner, *Free Radic. Res. Commun.* 1:349-53, 1986; Buettner and Jurkiewicz *Radiat. Res.* 145:532-41, 1996; Miller, et al., *Free Radic. Biol. Med.* 8:95-108, 1990). Metal cation-catalyzed oxidation of ascorbate can be conveniently monitored as a decrease in absorbance at 265 nm (Buettner *Free Radic. Res. Commun.* 10:5-9, 1990), as described in Example 8 and shown in FIGS. 5, 6, and 8. Certain chelating agents can appreciably slow down autooxidation of ascorbate at pH 7.0 or lower (Buettner *J. Biochem. Biophys. Methods* 16:27-40, 1988), as described in Example 10 and shown in FIG. 8.

In another embodiment, a composition of the present invention includes one or more chelators, one or more denaturing agents, and one or more antimicrobial agents, wherein the pH of the composition is within a pH range of about 6.0 to about 11.0, desirably at a pH of about 8.0. Microbial growth may also be inhibited by the strong chelators and denaturing agents, for example, ethanol, described above. Therefore, in a further embodiment of the present invention, a composition for preserving and/or recovering DNA from sputum includes one or more chelators and one or more denaturing agents, wherein at least one or more of the denaturing agents and/or chelating agents is present in amounts to act as an antimicrobial agent.

Reagents that indicate when a biological sample has been contacted with a composition of the invention can also be included as part of the composition. Desirable are those reagents that result in a visual color change of the composition solution upon mixing with the added sample. These reagents can function by reacting with any number of functional groups that are contained in biological samples, including, for example, amines, thiols, or glycosyl groups. Such colorimetric reagents are known to those skilled in the art and are chosen in such a manner that other components of the composition do not interfere with their effective usage.

Methods of the Invention

The present invention features methods of collecting, preserving, and recovering nucleic acids from sputum using a composition of the invention. The methods of the invention involve contacting a sputum sample from a subject with a composition of the invention and optionally mixing the resulting solution with a protease, such as pronase or proteinase K. Furthermore, some compositions of the invention feature a reducing agent that can facilitate the recovery of nucleic acids from composition/sample mixtures by decreasing the viscosity of these mixtures.

Accordingly, one aspect of the invention features a method of preserving a nucleic acid contained in sputum that includes the steps of obtaining sputum from a subject, and contacting the sputum with a composition of the invention, thus preserving the nucleic acid. Examples 1 and 2 describe the collection of saliva, both from subjects that can follow instructions and from those that can not.

The sputum is typically contacted with a composition of the invention upon collection or immediately after it is collected, and preferably not much later than about 1 hour after collection. This time can vary depending on storage conditions of the sputum after collection. For example, it could be indefinite if stored frozen or perhaps 1-2 days if stored at 4° C. A reducing agent can be in the preserving composition used, or added at a later time prior to nucleic acid isolation. Desirable reducing agent-containing compositions are those that are stable and retain a reducing capacity for more than a week, desirably for up to about 46 days, and most desirably for at least 46 days.

In an example (see Example 5), the results of which are presented in Table 1, saliva was collected and mixed with approximately an equal volume of a composition of the invention (see Example 3 for preparation), and analyzed for DNA content by PCR analysis at later timepoints.

TABLE 1

Estimated amounts of DNA in saliva samples*
Donor #

| 1 | 2 | 3 | 4 | 5 | 6 | 7 | 8 | 9 | 10 | 11 |
|---|---|---|---|---|---|---|---|---|----|----|
| Stim. saliva collected on 02Feb26, analyzed 64 days by the DNase method ||||||||||||
| 21.2 | 21.4 | 16.6 | 16.0 | 28.8 | | 44.8 | 22.2 | 16.6 | | |
| Unstim. saliva collected on 02Mar25, analyzed 15 days later by DNase method ||||||||||||
| | | 64.2 | | | | | 80.6 | 24.4 | 27.2 | 69.0 |

*DNA content in nanograms per microliter

To collect the sputum from the subject it is preferred that the mouth be rinsed before sampling. Food particles can introduce foreign DNA and saliva transferred by kissing can be a source of foreign human DNA. The mouth can be rinsed with about 50 mL of tepid water by vigorous swishing or by brushing with a tooth brush without tooth paste. Unstimulated saliva is usually of the mucinous type and is secreted at a slow rate. Stimulated saliva (anticipation of tasty food, sweet or sour candy) is of the serous (watery) type and secreted at a faster rate. It has been found (see Table 2) that there is more DNA in 2 mL of unstimulated saliva than 2 mL of stimulated saliva. After rinsing of the mouth and waiting about two or three minutes, the donor may spit a volume (for example, about 2 mL) of "unstimulated" saliva into the receiving tube. If this proves to be difficult, saliva flow can conveniently be stimulated with a cube of table sugar, or any other such saliva-stimulatory substance that does not interfere with DNA recovery or purification.

TABLE 2

Comparison of DNA content of unstimulated and stimulated saliva

| Donor #7 | unstimulated | stimulated |
|---|---|---|
| Collected on 2002 Apr. 6, analyzed 2 days later by the DNase method | 36.2* | 21.8* |

*Estimated amount of DNA in ng per μL of original undiluted saliva sample

Another aspect of the invention features a method of reducing the viscosity of a mucin-containing bodily fluid or tissue by reducing disulfide bonds inherent to mucin, wherein the bodily fluid or tissue is mixed with a composition of the invention that includes a reducing agent. In one embodiment, the bodily fluid is sputum, desirably saliva.

Yet another aspect of the invention features a method of recovering a nucleic acid from sputum that includes the steps of: i) obtaining sputum from a subject, ii) contacting the sputum with a composition of the invention to form a mixture, iii) contacting the mixture with a protease, and iv) recovering the nucleic acid from the mixture.

Suitable proteases include, for example, proteinase K or pronase. The protease may suitably be in a dry form that would become activated once mixed with sputum and a composition of the invention. In one embodiment, the protease is deposited onto an interior surface of the collection device. This can be accomplished by dissolving the protease in a solution made up of equal volumes of 5% sucrose in water and 5% glycerol in ethanol and then, after placing the solution on the surface, removing the volatiles under a controlled vacuum to leave the protease bound to the surface as a sticky residue. If the composition does not contain a reducing agent (or even if it does), a reducing agent can be added at any time prior to isolation of the nucleic from the sample, desirably prior to or concurrently with contacting the sample with a suitable protease.

When sputum is mixed with a composition of the present invention, cells are disrupted, nucleic acids are liberated from the cells, membranous material is solubilized, proteins are stripped from the nucleic acids, and protein digestion begins. If present, a reducing agent in the composition reduces the viscosity of the gel-forming mucin. Incubation can be at room temperature over a relatively long period of time (days or weeks) while samples are being shipped to a laboratory for analysis. If transferred to a laboratory soon after collection, incubation at 55° C. for 4 to 16 hours is sufficient to allow the activated protease to digest the majority of protein to small peptides or amino acids. Under such conditions, nucleic acids and polysaccharides remain relatively intact.

Once digestion is complete, nucleic acid isolation can be performed using any technique known in the art (*Short Protocols in Molecular Biology,* 5th Edition Frederick M. Ausubel, Roger Brent, Robert E. Kingston, David D. Moore, J. G. Seidman, John A. Smith (Editor), Kevin Struhl (Editors). ISBN: 0-471-25092-9. 2002. John Wiley and Sons). In one example, in which SDS is used as a denaturant component of the composition, a "precipitation solution" consisting of, for example, potassium chloride may be added to a portion of the sputum-composition mixture resulting in the precipitation of potassium dodecyl sulfate, after standing on ice to cool the solution. Following a short period of centrifugation to remove the precipitate and any residual insoluble material, the supernatant is collected. At this stage, the supernatant is expected to contain as much as 10-30 nanograms per microliter of DNA. For analyses where as little as 1 nanogram of DNA is sufficient, the sample can be diluted.

When larger amounts of DNA are required, the DNA in the supernatant can be precipitated by the addition of alcohol and redissolved in any suitable buffer. This step has the effect of removing inhibitory components of the composition, which are present to preserve the nucleic acids during transport to the laboratory.

If more highly purified DNA is required, then other known purification steps can be used (*Short Protocols in Molecular Biology,* 5th Edition Frederick M. Ausubel, Roger Brent, Robert E. Kingston, David D. Moore, J. G. Seidman, John A. Smith (Editor), Kevin Struhl (Editors). ISBN: 0-471-25092-9. 2002. John Wiley and Sons), such as extraction with phenol or solid-phase extraction. It should be noted that, because the DNA is in a relatively pure state using the procedures described above, any additional purification steps are made easier when compared to analogous purifications of DNA originating from a blood sample.

The methods of the present invention can be used to isolate nucleic acids from sputum for any application requiring a nucleic acid sample. For example, some specific applications of the methods of the present invention include, but are not limited to, forensic applications, medical applications (including genetic screening and disease typing), and paternity testing.

Another aspect of the invention features a method of preserving and/or recovering a nucleic acid from a bodily fluid that includes, placing the bodily fluid into a first region of a container, placing a composition of the invention into a second region of the container, which is separated from the first region by a barrier, closing the container, and disturbing the integrity of the barrier such that the composition and the bodily fluid are brought into contact. Collection devices of the invention, which also can serve as containers for bring the compositions and nucleic acid-containing bodily fluids together are described below.

Collection Devices

The invention also provides a novel collection device useful for collecting a biological sample from a subject, and subsequently mixing the collected sample with a composition intended to stabilize, preserve, or facilitate the recovery of components of the sample. Such components may include, without limiting the invention, nucleic acids, proteins, peptides, toxins, chitins, fatty acids, and glycogens. Non-limiting examples of biological samples are skin, hair, fecal matter, bodily fluids, and tissue.

Desirably, the invention features a device for preserving and/or recovering a nucleic acid obtained from a biological sample. The device includes: a container that has a first region for collecting a biological sample and a second region containing a composition for preserving a nucleic acid, a barrier between a first region and a second region that keeps the sample and composition separate, a means for closing the container, and a means for disturbing the integrity of the barrier, such that the composition is capable of contacting the bodily sample. In one embodiment, the composition is a composition of the present invention. In another embodiment, the sample is a biological fluid.

The collection device of the invention simultaneously serves several functions. Some of the desirable features of this collection vessel include one or more of the following:

a) it may be constructed of a sturdy breakage-resistant plastic, desirably a biocompatible plastic. Desirably, the container would be constructed from a material that would not leach chemicals into the container's contents;

b) it would have a broad mouth that would make it relatively simple for a subject to place the required volume of fluid sample, desirably expectorated sputum, and most desirably expectorated saliva, into the device's container;

c) the bottom part of the container would be narrow to reduce the overall volume of the container to make it easier to collect the small volume (1-2 milliliters) of fluid that would be expected from a routine sampling, in particular, when the sample is an expectorate. Optionally, the device would contain markings to allow for an estimate of the sample volume collected;

d) the means for closing the container may be a cap that is designed to lock once tightened to become tamper-resistant;

e) the means for closing the container may be a cap that is designed to provide a liquid-tight and/or airtight seal for the container once the cap is fixed into place;

f) the barrier may be a septum or plastic bag compact lent that would separate the composition from the fluid until the septum or bag compartment is pierced or the contents otherwise released;

g) the barrier may be in the form of a pivoting partition. In this embodiment, attachment of the lid to the container forces the partition to pivot from its original position of spanning the space between the first region and the second region to a position in which both regions are exposed to each other and contact between the composition contained in one space and the bodily fluid contained in the other space is allowed;

h) the barrier can be press fit, glued, or heat fit into place;

i) the means for closing the container may be coupled to the disestablishment of the barrier; and j) an antimicrobial agent that coats the outside of the device.

Figure 10:
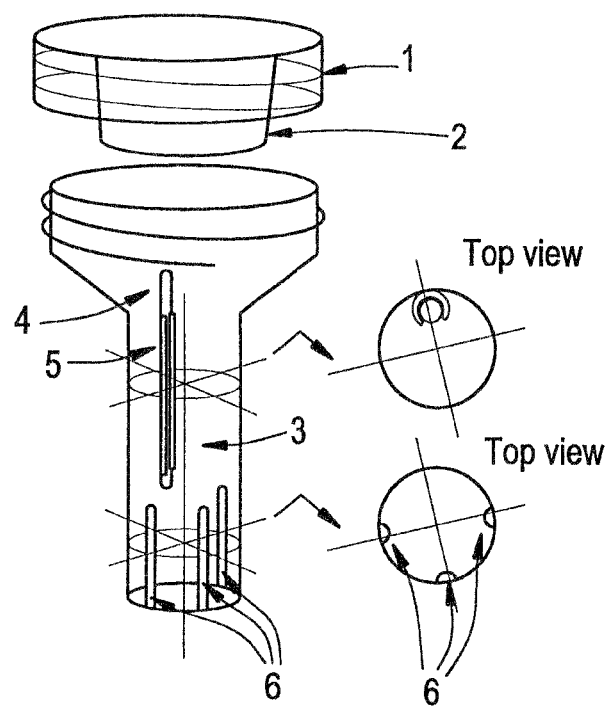
FIG. 10 is an exploded view of a sample container of the invention. Included in the figure is a cross-sectional top view taken at line 1-1 of container 3 showing plunger 4 and plunger channel 5. Also shown is a cross-sectional top view taken at line 2-2 of container 3, showing supports 6 for sealing disc 7 (not shown in this figure but shown in FIG. 11).
Figure 11:
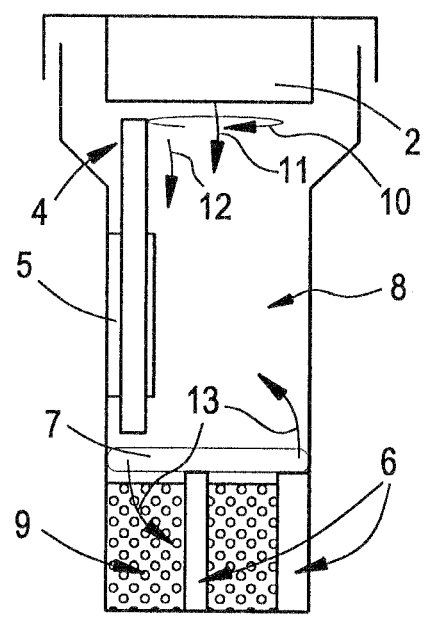
FIG. 11 is a side view of the sample container of FIG. 10, now showing sealing disc 7.

A device of the invention is shown in FIGS. 10 and 11. With cap 1 not attached to the device, a biological sample (not shown) is applied to a first region 8 of container 3, which is separated from a second region 9 by sealing disc 7. After sample application, cap 1 is placed onto the device and secured via a screw thread mechanism to a tight fit, thereby sealing container 3. As the cap is twisted on (shown by dotted line and arrow 10, ram 2, which is attached to cap 1, moves downward as shown by dotted line arrow 11. This downward movement forces plunger 4, which is contained in plunger barrel 5, downward as indicated by dotted line and arrow 12. The downward movement of plunger 4 forces sealing disc 7 to pivot, as shown by dotted line and arrow 13. Pivoting of disc 7 disestablishes the barrier between regions 8 and 9, thereby permitting contact between the sample and a composition of the invention, shown as a dotted solution contained in region 9.

Kits

The present invention also features kits for performing the methods of the invention that include a device of the invention containing a composition of the invention, with instructions for stabilizing, preserving, or facilitating the recovery of nucleic acids from a biological sample by using the device to bring a biological sample into contact with the composition.

EXAMPLES

Example 1

Protocol for Obtaining Saliva Samples from Subjects Capable of Following Instructions The subject is instructed to wait for a period of 20-30 minutes before last eating. The subject will brush his teeth without using toothpaste, if possible. The subject will rinse his mouth vigorously with 50 mL of cool or tepid water. The subject will then spit saliva into the special collection tube until the level of saliva reaches the 2 mL mark. This may take several minutes. If the subject finds that he is unable to deliver sufficient saliva, he will be given a cube of table sugar to chew, and told not to be concerned if some of the sugar is spit into the tube.

When the required amount of saliva is collected, it is mixed with 2 mL of a nucleic acid-preserving composition. The precise way this will be introduced will depend upon the container design.

Once the composition is introduced, the cap is attached to the container and tightened to seal it securely. The container is then vigorously shaken and the process is complete. The DNA is now in an intermediate preserved state. It can be maintained in a frozen state or at any temperature up to about 60° C.

The container can be mailed back to the testing lab at room temperature.

Example 2

Protocol for Obtaining Saliva Samples from Babies, Very Young Children and Infirm Adults Incapable of Following Instructions A rubber or plastic tube or nipple will be introduced into the mouth, attached to a sponge, suction bulb or small syringe, and kept in the mouth for several minutes until visible drooling occurs. A bit of sugar cube will be placed in the mouth to stimulate saliva if necessary. The responsible adult will wear disposable gloves provided for the purpose to avoid contamination with his/her DNA. The responsible adult will draw saliva into the bulb or syringe and transfer it into the collection container. The DNA preserving/extraction composition is introduced and the container is capped and sealed. The tube is vigorously shaken for 1 minute.

Example 3

Preparation of a Nucleic Acid-Preserving Composition

The composition of the nucleic acid-preserving solution used in Examples 4-6 is 33 mM TRIS-HCl, 0.67 M urea, 0.67 M LiCl, 0.6% sodium dodecyl sulfate, 3.3 mM CDTA, 30% ethanol, and 0.25 M sodium ascorbate, all adjusted to a final pH of 8.0. In the examples, the composition is mixed with an equal volume of saliva. Subsequent to these experiments, it has been found that a composition which is 0.3 M TRIS-HCl, 0.67 M urea, 0.67 M NaOAc, 0.6% sodium dodecyl sulfate, 3.3 mM CDTA, 30% ethanol, and 0.1 M sodium ascorbate, all adjusted to a final pH of 8.0, stabilizes DNA for longer periods of time.

Example 4

Extration of Minimally Purified Chromosomal DNA from the Stimulated Saliva of 8 Different Donors After collection of saliva in an equal volume of the composition as noted in Example 3, followed by 14 days storage at room temperature, a 0.25 mL portion of each donor's sample was treated with proteinase K, centrifuged briefly to remove insoluble material and the DNA therein was precipitated with 2 volumes of ethanol. The precipitate was dissolved in 0.05 mL of water, and an 8 µL aliquot (equivalent to about 20 µL of undiluted saliva) was analyzed by electrophoresis on a 0.8% agarose gel, stained with ethidium bromide to visualize the DNA (see FIG. 1). Of note is the characteristic band of chromosomal DNA present in all samples at the position of the arrow, that corresponds to the position of chromosomal DNA extracted from white blood cells (data not shown).

Example 5

"Real Time" Polymerase Chain Reaction Using DNA from Stimulated Saliva

Figure 2:
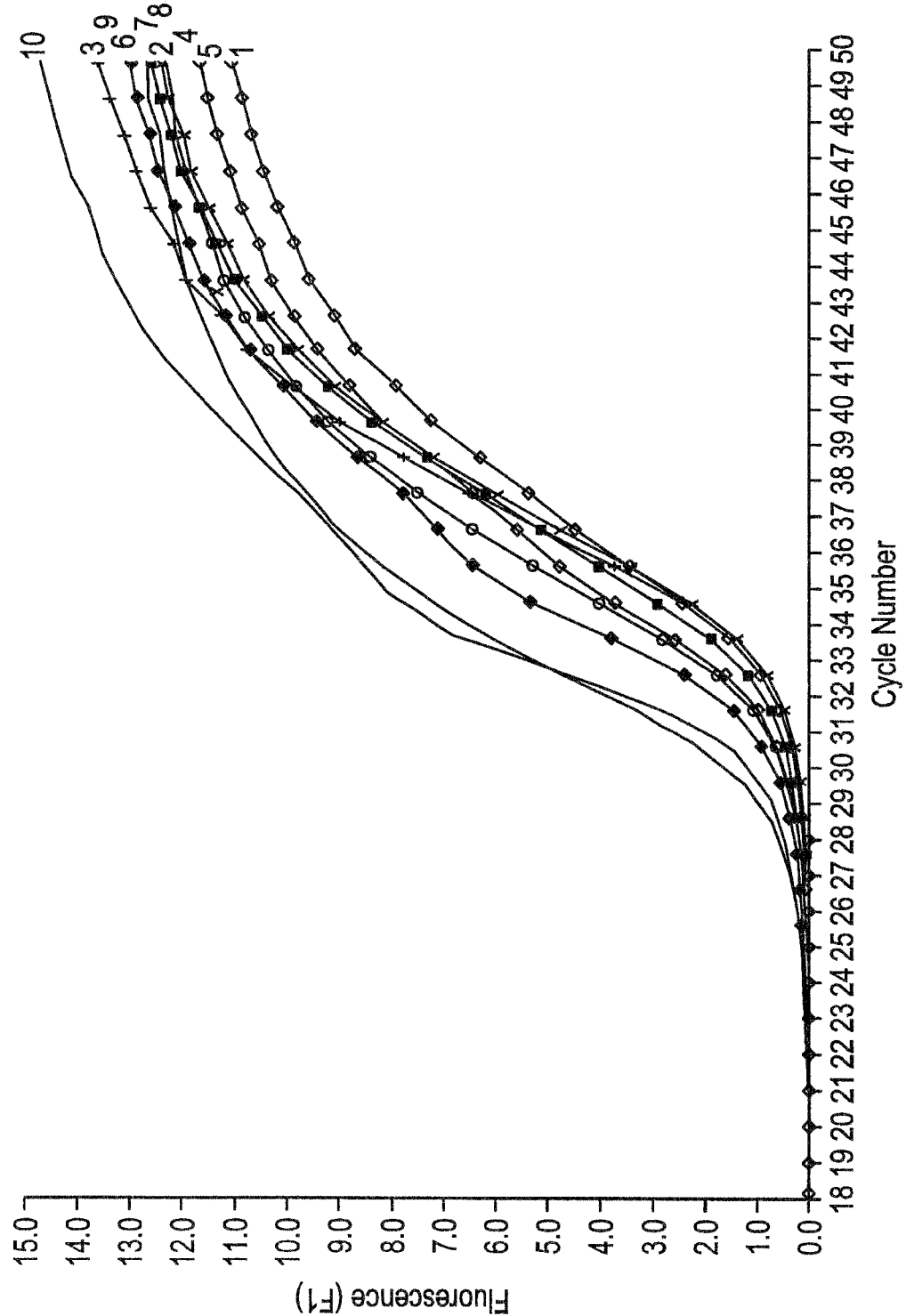
FIG. 2 is a graph illustrating real time PCR of stimulated saliva DNA of Example 5.

Stimulated saliva samples collected on 26 Feb. 2002 (see Table 1) and stored at room temperature were analyzed 62 days later. Minimally purified DNA was prepared as follows: an aliquot was centrifuged to remove insoluble material; to the clarified supernatant was added 2 volumes of ethanol; the precipitate containing DNA was collected by centrifugation and redissolved in water. A volume of the redissolved DNA equivalent to 0.05 microliters of each of the original saliva samples was used for analysis. Real time PCR was carried out using a Roche Light Cycler instrument, where the fluorescent dye SYBR green I was added to follow the reaction (see results of FIG. 2). The primers were designed to detect the human Clotting Factor IX gene (Grant, et al., *J. Immunol. Methods* 225:61-6, 1999). C=control, highly purifed white blood cell DNA. Each curve represents results using saliva DNA from different donors, represented by a number. These results using real time PCR demonstrate the suitability of minimally purified saliva DNA from different donors for PCR analysis.

Example 6

"Real Time" Polymerase Chain Reaction Using DNA from Unstimulated Saliva

Figure 3:
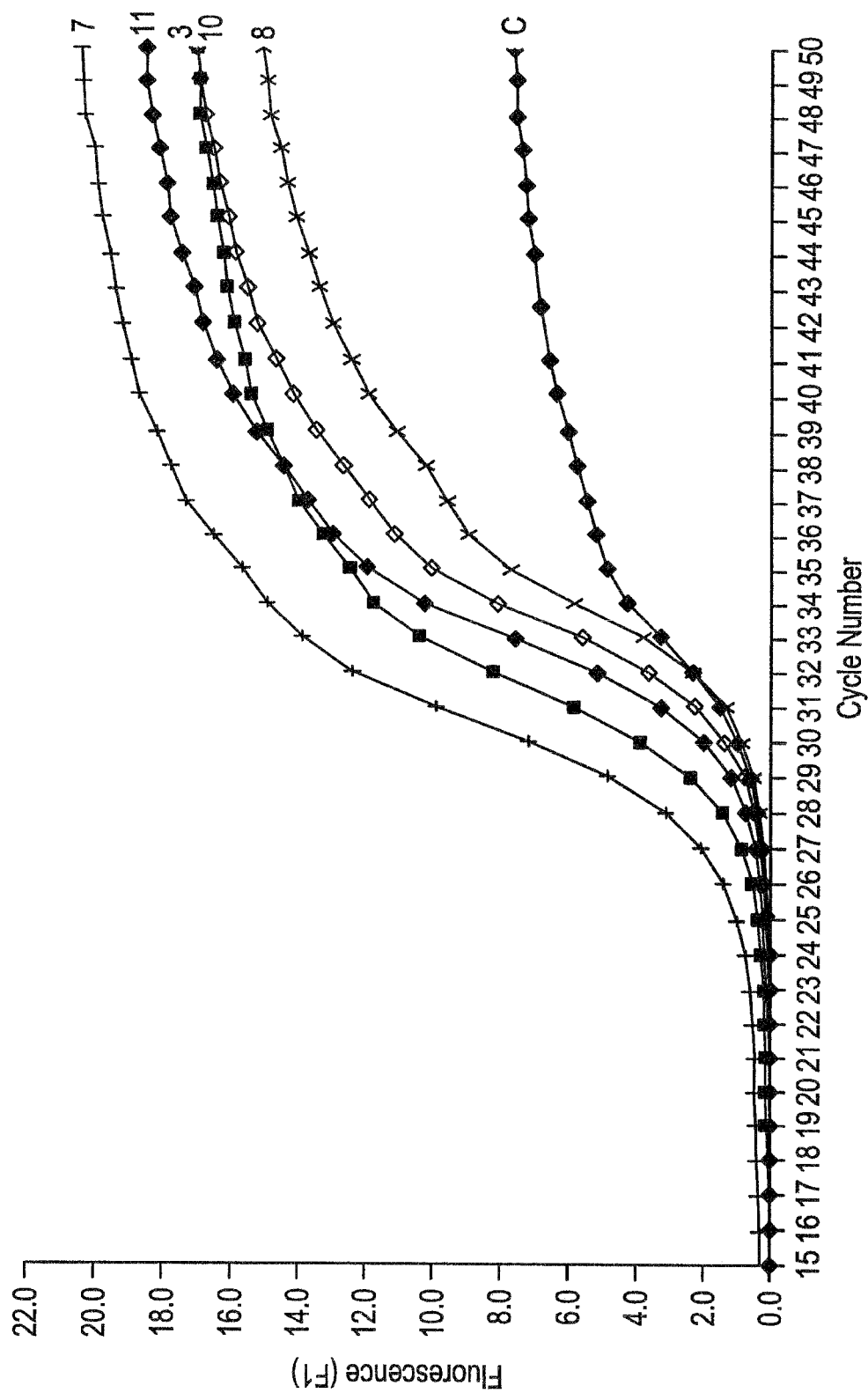
FIG. 3 is a graph illustrating real time PCR of unstimulated saliva DNA of Example 6.
Figure 4:
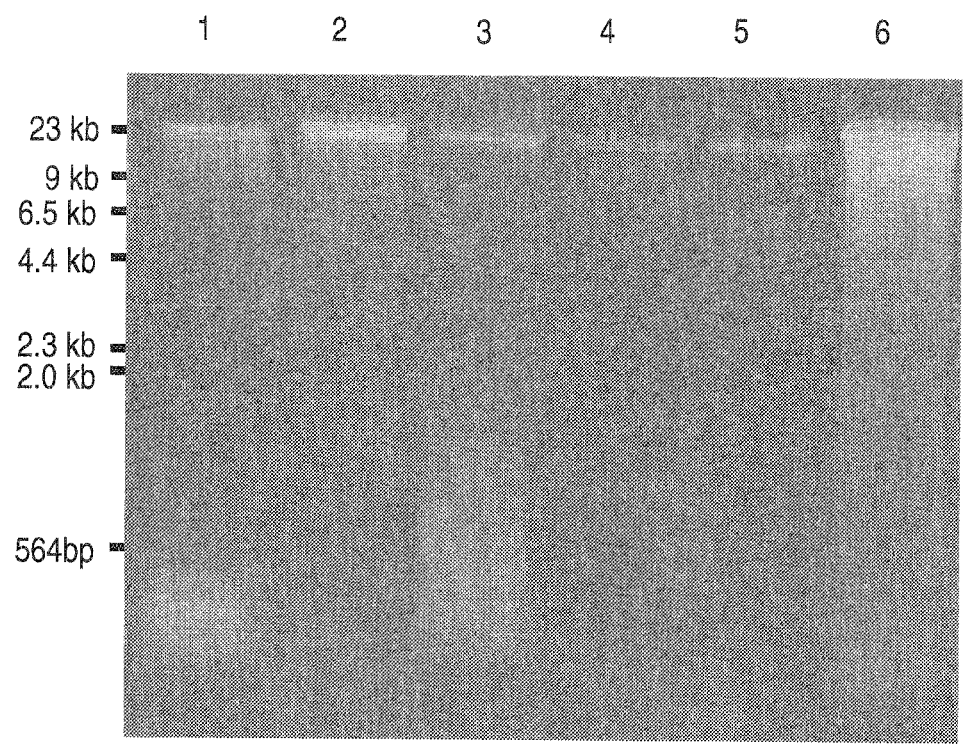
FIG. 4 is an electrophoresis agarose analysis of the DNA in saliva samples mixed with compositions of the invention, the mixtures having been incubated for various times at various temperatures.

FIG. 3 is a graph showing saliva DNA samples collected on 2002 Mar. 25 (see Table 1) and analyzed on 30 days later in accordance with FIG. 1. Minimally purified DNA was used Polymerase chain reaction and other conditions as described in Examples 4 and 5 except saliva collection was done under unstimulated conditions. Numbers refer to individual donors. C is control DNA, a highly purified sample of DNA purified from blood.

Tables 1 and 2 show estimates of DNA recovered from saliva samples. In all cases, the individual donor has been identified by a unique number. These data show that the amount of DNA that can be recovered from this group of donors ranges from 16 micrograms per milliliter of saliva and higher. Estimation of the amount of DNA by chemical methods such as DABA presents some problems and the DNase method provides most reliable results.

Example 7

Stability Studies on DNA from Saliva

Saliva was mixed with an equal volume of the indicated composition and the mixture was incubated for the indicated time period at the indicated temperature (see Table 3). After incubation, approximately 40 µL of mixture was digested briefly with ribonuclease to remove the majority of the RNA present in the sample, then applied to the indicated lane of a 0.8% agarose gel. Following electrophoresis, the gel was stained with ethidium bromide as in Example 4.

TABLE 3

| Lane No. | Composition | Incubation Conditions |
| --- | --- | --- |
| 1 | 0.5M NaOAc, 0.2M TRIS-HCl, 0.15M Na ascorbate, 10 mM CDTA, 1% SDS, 30% (v/v) ethanol, pH = 9.5 | 70° C. for 3 days, then 50° C. for 16 days |
| 2 | 0.5M NaOAc, 0.2M TRIS-HCl, 10 mM CDTA, 1% SDS, 30% (v/v) ethanol, pH = 9.5 | 50° C. for 21 days |
| 3 | 0.5M NaOAc, 0.2M TRIS-HCl, 10 mM CDTA, 1% SDS, 30% (v/v) ethanol, pH = 9.5 | 70° C. for 3 days, then 50° C. for 31 days |
| 4 | 0.67M LiCl, 33 mM TRIS-HCl, 0.67M urea, 0.6% SDS, 3.3 mM CDTA, 30% (v/v) ethanol, pH = 8.0 | 20° C.-25° C. for 15 months |
| 5 | 0.67M LiCl, 33 mM TRIS-HCl, 0.67M urea, 0.6% SDS, 3.3 mM CDTA, 30% (v/v) ethanol, pH = 8.0 | 20° C.-25° C. for 15 months |
| 6 | Control chromosomal DNA prepared from white blood cells | |

Example 8

Rapid Autooxidation of Ascorbate in the Presence of a Transition Metal Ion

A solution of sodium ascorbate (100 µM) in CB (10 mM BES, pH 7.4, containing 1 mM CDTA) was freshly prepared under aerobic (equilibrated with ambient air) conditions. Several spectrophotometric scans over 30 minutes at room temperature showed no change in the absorbance profile (all similar to scan (1)). Scan (2) was taken 3 minutes after addition of a few crystals of $MnCl_2$. The results can be seen in FIG. 6. As shown, 100 µM ascorbate at neutral pH has an absorbance ($\lambda_{max}$=265 nm) of about 1.25 (corresponding to the expected molar extinction coefficient ($A_M$) of about 12,500. Upon addition, the transition metal, manganous chloride, catalyzed the autooxidation of ascorbate, which can conveniently be monitored by a decrease in absorbance at $\lambda$=265 nm (Buettner, *Free Radic. Res. Commun.* 10:5-9, 1990).

Example 9

Spontaneous Autooxidation of Ascorbate

Figure 7:
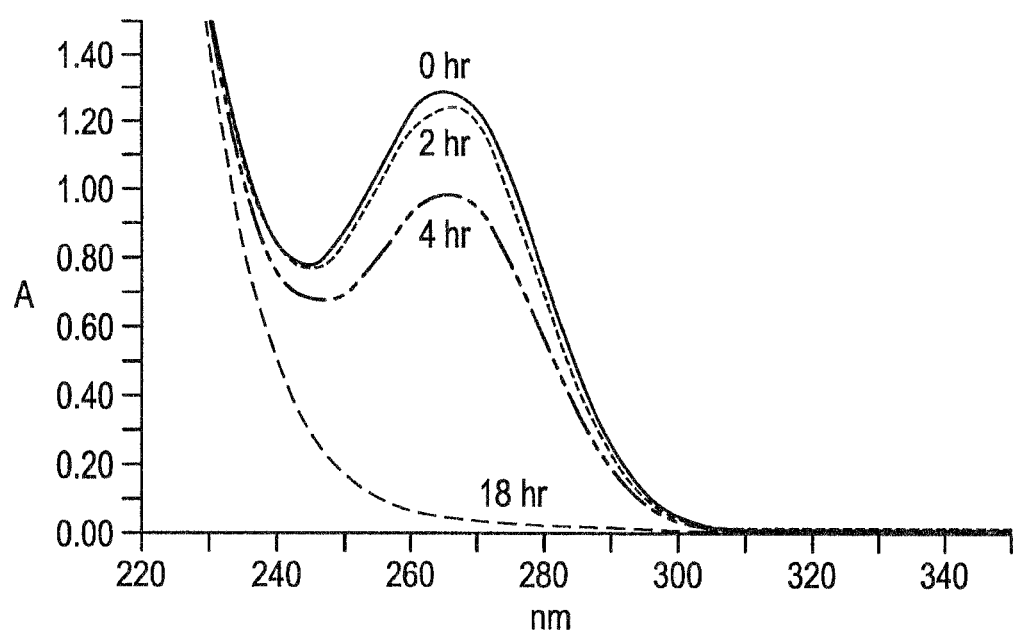
FIG. 7 is a compilation of spectrophotometric scans, at the indicated times, of the 100 μM sodium ascorbate prepared in CB of Example 8. The solution was exposed to ambient atmosphere and temperature between scans but was not contacted with $MnCl_2$ (see Example 9).

Repeated scans at the indicated time points were taken of an aliquot of the 100 µM sodium ascorbate solution prepared in Example 8, before the addition of MnCl$_2$. The sample was exposed to air and maintained at room temperature between scans. The results are illustrated in FIG. 7, and indicate that autooxidation of ascorbate occurs at pH 7.4 can occur over an extended period of time in the presence of low concentrations (1 mM) of CDTA, a "strong" chelator.

Example 10

Stability of Sodium Ascorbate in a Nucleic Acid-Preserving Composition

Figure 8:
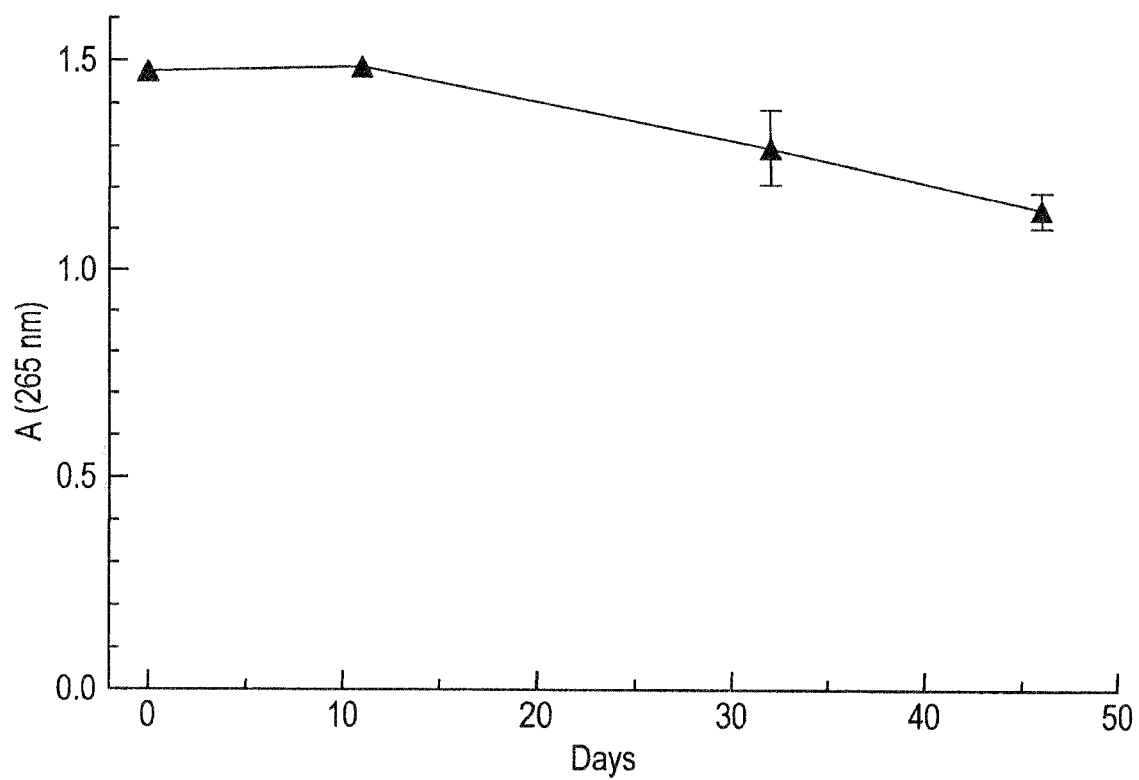
FIG. 8 is a graph of absorbances at 265 nm, obtained at the indicated times, of a solution of sodium ascorbate (250 mM) containing 30 mM Tris-HCl, pH 8.0, 30% ethanol, 3 mM CDTA, mixed with 50 mL of CB, as per Example 10. The stock solution was maintained at room temperature and no precaution was taken to exclude ambient atmosphere or ambient light.
Figure 9:
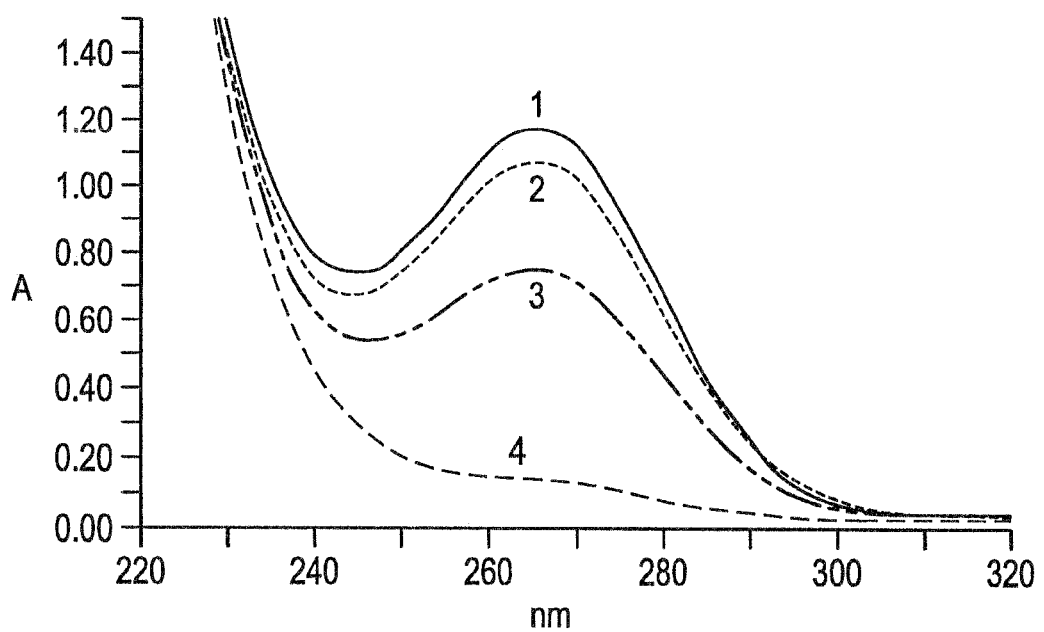
FIG. 9 is a compilation of spectrophotometric scans of the 46 day-old solution prepared in Example 10. Scan 1 (t=46 days) was taken before the addition of $MnCl_2$. Scan 2 was taken 2 minutes after the addition $MnCl_2$. Scan 3 was taken 8 minutes after the addition $MnCl_2$. Scan 4 was taken 27 minutes after the addition $MnCl_2$.

A stock solution of sodium ascorbate (250 mM) was prepared in a solution containing 30 mM Tris-HCl, pH 8.0, 30% ethanol, 3 mM CDTA. 20 µL was removed at the indicated times, mixed with 50 mL of CB (see Example 8) and the absorbance at 265 nm was read immediately. The stock solution was maintained at room temperature. The results are shown in FIG. 8.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A device for receiving and preserving nucleic acid in a biological sample, said device comprising:
   a. one or more walls defining a containment vessel having a top having an opening, and a closed bottom having a sample receiving area for holding said biological sample, said opening for receiving a liquid sample and for sealably receiving a sealing cap, said top having an opening for receiving a biological sample from the mouth of a user and further comprising at least one marking on said one or more walls which corresponds to a fluid volume in the sample receiving area;
   b. a reagent compartment having a barrier, said barrier sealing and containing reagents in said reagent compartment and capable of disestablishment to release said reagents into the sample receiving area;
   c. reagents in the reagent compartment for preserving nucleic acids potentially present in the sample wherein said reagents comprise a denaturing agent, a chelator and a buffer agent; and,
   d. the sealing cap, whereby the device is configured such that, when sealably closing said opening with said sealing cap, the barrier mechanically disestablishes to release said reagents to form a mixture of reagents and said biological sample wherein said buffering agent maintains a pH of said mixture equal to or above 5.0 to preserve nucleic acids potentially present in the sample.

2. The device of claim 1, wherein the biological sample comprises a bodily fluid.

3. The device of claim 1, wherein the biological sample comprises sputum.

4. The device of claim 1, wherein the biological sample comprises saliva.

5. The device of claim 1, wherein the denaturing agent comprises dodecyl sulfate.

6. The device of claim 1, wherein the chelator comprises ethylenediamine tetraacetic acid (EDTA).

7. The device of claim 1, wherein the reagents further comprise an antimicrobial agent.

8. The device of claim 1, wherein the reagents further comprise an antioxidant free-radical scavenger.

9. The device of claim 1, wherein the barrier comprises a septum.

10. The device of claim 9, wherein the septum is configured to be punctured or pierced to release the reagents to form a mixture of the released reagents and the biological sample.

11. The device of claim 10, wherein the biological sample comprises saliva.

12. The device of claim 11, wherein the denaturing agent comprises dodecyl sulfate.

13. The device of claim 12, wherein the chelator comprises ethylenediamine tetraacetic acid (EDTA).

14. The device of claim 13, wherein the buffering agent comprises TRIS.

15. The device of claim 14, wherein the buffering agent maintains pH of the mixture from about 7.0 and about 10.0.

16. The device of claim 15, wherein the reagents further comprise an antimicrobial agent.

17. The device of claim 16, wherein the reagents further comprise an antioxidant free-radical scavenger.

18. The device of claim 1, wherein the device is configured such that, upon sealably closing said opening with said sealing cap, the barrier is capable of permanent disestablishment.

19. The device of claim 1, wherein the device is configured such that, upon sealably closing said opening with said sealing cap, the barrier is permanently disestablished.

20. The device of claim 1, wherein the device is configured such that, upon sealably closing said opening with said sealing cap, the barrier displaces.

21. The device of claim 20, wherein the barrier is configured to disestablish when displaced by a linear actuator.

22. The device of claim 21, wherein the linear actuator comprises a plunger.

23. The device of claim 1, wherein sealably receiving the sealing cap comprises engaging a thread on the sealing cap and the opening.

24. The device of claim 23, wherein engaging the thread on the sealing cap and the opening comprises exerting a force on the barrier, wherein the force is perpendicular to a direction of rotation of the sealing cap.

25. The device of claim 24, wherein exerting the force on the barrier comprises displacing the barrier.

26. The device of claim 24, wherein a linear actuator exerts the force on the barrier.

27. The device of claim 1, wherein the barrier remains in a disestablished position while the opening is sealably closed by the sealing cap.

28. The device of claim 27, wherein the barrier is capable of returning to a pre-disestablished position when the sealing cap is not sealably closing the opening.

29. The device of claim 27, wherein the barrier is configured to be displaced from a pre-disestablished position to a disestablished position when sealably closing the opening with the sealing cap.

30. The device of claim 1, wherein the barrier remains intact when disestablished.

31. The device of claim 1, wherein sealably receiving the sealing capa comprises engaging the containment vessel and the barrier.

32. The device of claim 31, wherein engaging the containment vessel and the barrier comprises engaging the sealing cap and a plunger, thereby engaging the plunger and the barrier.

33. The device of claim 1, wherein the barrier is configured to disestablish at room temperature.

34. The device of claim 1, wherein the sealing cap associates with the containment vessel to create a fluid-tight seal.

35. The device of claim 1, wherein at least partially dissociating the sealing cap from the containment vessel causes the barrier to close.

36. The device of claim 10, wherein the device further comprises a piercing member and wherein the piercing member is configured to puncture or pierce the septum to release the reagents to form a mixture of the released reagents and the biological sample.

* * * * *